(12) United States Patent
Knopp et al.

(10) Patent No.: US 7,499,159 B2
(45) Date of Patent: Mar. 3, 2009

(54) METHOD AND APPARATUS FOR CONDUCTING RAMAN SPECTROSCOPY USING A REMOTE OPTICAL PROBE

(75) Inventors: Kevin J. Knopp, Newburyport, MA (US); Leyun Zhu, Andover, MA (US); Daryoosh Vakhshoori, Cambridge, MA (US)

(73) Assignee: Ahura Corporation, Wilmington, MA (US)

( * ) Notice: Subject to any disclaimer, the term of this patent is extended or adjusted under 35 U.S.C. 154(b) by 93 days.

(21) Appl. No.: 11/484,534

(22) Filed: Jul. 11, 2006

(65) Prior Publication Data

US 2007/0024848 A1    Feb. 1, 2007

Related U.S. Application Data

(63) Continuation-in-part of application No. 10/826,706, filed on Apr. 16, 2004, now Pat. No. 7,110,109, and a continuation-in-part of application No. 11/117,940, filed on Apr. 29, 2005.

(60) Provisional application No. 60/698,270, filed on Jul. 11, 2005.

(51) Int. Cl.
*G01J 3/44* (2006.01)
*G01N 21/65* (2006.01)
*G02B 6/32* (2006.01)

(52) U.S. Cl. ......................... 356/301; 385/125
(58) Field of Classification Search ................. 356/301; 385/125
See application file for complete search history.

(56) References Cited

U.S. PATENT DOCUMENTS

| | | | |
|---|---|---|---|
| 3,017,513 A | | 1/1962 | Messelt |
| 3,906,241 A | | 9/1975 | Thompson |
| 4,045,119 A | * | 8/1977 | Eastgate ..................... 385/125 |
| 5,026,160 A | | 6/1991 | Dorain et al. |
| 5,048,959 A | | 9/1991 | Morris et al. |
| 5,483,337 A | | 1/1996 | Barnard et al. |
| 5,651,018 A | | 7/1997 | Mehuys et al. |
| 5,675,689 A | * | 10/1997 | Nath ......................... 385/125 |

(Continued)

FOREIGN PATENT DOCUMENTS

WO    WO 02/101365 A1 * 12/2002

OTHER PUBLICATIONS

Eckenrode, Brian A. et al., Portable Raman Spectroscopy Systems for Field Analysis, Forensic Science Communications, Oct. 2001, vol. 3, No. 4.

(Continued)

*Primary Examiner*—F. L Evans
(74) *Attorney, Agent, or Firm*—Fish & Richardson P.C.

(57) ABSTRACT

An optical probe assembly includes a light guide that includes a core region and a surrounding cladding region. The core region is constructed so as to minimize the creation of a relatively broadband spurious background noise signal when conveying the Raman pump light to the specimen, and the cladding region is constructed so as to satisfy the wave guiding reflection requirements of the Raman pump light and the Raman signature. A Raman spectroscopy system includes: a laser for producing Raman pump light; an optical probe assembly; and an optical spectrum analyzer for receiving the Raman signature of a specimen and identifying and characterizing the specimen based upon the spectrum of the Raman signature. Related methods are also disclosed.

33 Claims, 5 Drawing Sheets

Probe Cross Section

U.S. PATENT DOCUMENTS

| | | |
|---|---|---|
| 5,734,165 A | 3/1998 | Unal et al. |
| 5,828,450 A | 10/1998 | Dou et al. |
| 6,069,689 A | 5/2000 | Zeng et al. |
| 6,249,349 B1 | 6/2001 | Lauer |
| 6,303,934 B1 | 10/2001 | Daly et al. |
| 6,608,677 B1 | 8/2003 | Ray et al. |
| 6,803,328 B2 | 10/2004 | McCullough |
| 6,862,092 B1 | 3/2005 | Ibsen et al. |
| 6,977,723 B2 | 12/2005 | Lemmo et al. |
| 2002/0033944 A1 | 3/2002 | Sharts et al. |
| 2003/0002548 A1 | 1/2003 | Boscha |
| 2003/0002839 A1 | 1/2003 | Clow et al. |
| 2003/0085348 A1 | 5/2003 | Megerle |
| 2003/0197860 A1 | 10/2003 | Rice |
| 2004/0039274 A1 | 2/2004 | Benaron et al. |
| 2004/0109230 A1 | 6/2004 | Matsushita et al. |
| 2004/0165183 A1 | 8/2004 | Marquardt et al. |
| 2004/0165254 A1 | 8/2004 | Tokura et al. |
| 2004/0252299 A9 | 12/2004 | Lemmo et al. |
| 2004/0263843 A1 | 12/2004 | Knopp et al. |
| 2005/0083521 A1 | 4/2005 | Kamerman |
| 2006/0023209 A1 | 2/2006 | Lee et al. |
| 2006/0170917 A1 | 8/2006 | Vakhshoori et al. |

OTHER PUBLICATIONS

Harvey, S.D. et al., Blind field test evaluation of Raman spectroscopy as a forensic tool, Forensic Science International, 2002, 12-21, 125.

Moore, D.S., Instrumentation for trace detection of high explosives, Aug. 2004, 2499-2512, vol. 75, No. 8.

* cited by examiner

METHOD AND APPARATUS FOR CONDUCTING RAMAN SPECTROSCOPY USING A REMOTE OPTICAL PROBE

REFERENCE TO PENDING PRIOR PATENT APPLICATION

This patent application:

(i) is a continuation-in-part of prior U.S. patent application Ser. No. 10/826,706, filed Apr. 16, 2004 now U.S. Pat. No. 7,110,109 by Kevin J. Knopp et al. for RAMAN SPECTROSCOPY SYSTEM AND METHOD AND SPECIMEN HOLDER THEREFOR;

(ii) is a continuation-in-part of pending prior U.S. patent application Ser. No. 11/117,940, filed Apr. 29, 2005 by Peidong Wang et al. for METHOD AND APPARATUS FOR CONDUCTING RAMAN SPECTROSCOPY; and (iii) claims benefit of prior U.S. Provisional Patent Application Ser. No. 60/698,270, filed Jul. 11, 2005 by Kevin J. Knopp et al. for DISPOSABLE OPTICAL PROBE FOR RAMAN SPECTROSCOPY.

The three above-identified patent applications are hereby incorporated herein by reference.

FIELD OF THE INVENTION

This invention relates to methods and apparatus for identifying and characterizing substances in general, and more particularly to methods and apparatus for identifying and characterizing substances using Raman spectroscopy.

BACKGROUND OF THE INVENTION

Raman spectroscopy is an effective tool for identifying and characterizing a vast array of substances.

In Raman spectroscopy, laser light of a known wavelength (typically infrared or near infrared) is directed at a specimen. The laser light (also sometimes referred to as the Raman pump) interacts with the electron clouds in the molecules of the specimen and, as a result of this interaction, experiences selected wavelength shifting. The precise nature of this wavelength shifting depends upon the materials present in the specimen. A unique wavelength signature (typically called the Raman signature) is produced by each specimen. This unique Raman signature permits the specimen to be identified and characterized. More specifically, the spectrum of light returning from the specimen is analyzed with a spectrometer so as to identify the Raman-induced wavelength shifting in the Raman pump light, and then this wavelength signature is compared (e.g., by a computer) with a library of known Raman signatures, whereby to identify the precise nature of the specimen.

Raman spectroscopy is widely used in scientific, commercial and public safety areas.

Recent technological advances have made it possible to significantly reduce the size and cost of Raman spectroscopy systems. This has in turn increased the range of practical applications for Raman spectroscopy. For example, portable units have recently become available for various field uses, such as the on-site identification of potentially hazardous substances.

In some instances it can be desirable for the Raman spectroscopy system to have its optical probe head (i.e., the light launch and collector portions of the system) separated from the main body of the Raman system (e.g., the laser, spectrometer, computer, etc.). For example, this can be useful in situations where the entire Raman spectroscopy system will not conveniently fit adjacent to the specimen. In this case, the optical probe head is typically connected to the main body of the Raman system by a flexible optical connector.

Additionally, in some instances it can be desirable for the optical probe head to be disposable. For example, where specimen purity is of concern, or where the specimen may be highly toxic, it may be desirable for the optical probe head to be replaced after use.

As noted above, where the Raman spectroscopy system has its optical probe head separated from the main body of the Raman system, the optical probe head is typically connected to the main body of the Raman system by a flexible optical connector. This flexible optical connector generally comprises a long, thin light guide, or guides, to deliver the excitation light to the specimen and to collect the Raman signature from the specimen. It is also generally desirable that the light guide, or guides, be flexible, rugged, and compact.

Conventional optical fibers have traditionally been used as the light guide(s) to deliver the excitation light to the specimen and to collect the Raman signature from the specimen. However, the amorphous nature of the glass used in a conventional optical fiber (and, specifically, the non-linear coefficients of the optical fiber's refractive index), together with the high optical power of the pump laser, typically causes a relatively broadband spurious background noise signal, having a significant intensity, to be generated as the pump light travels through the fiber.

Figure 1:
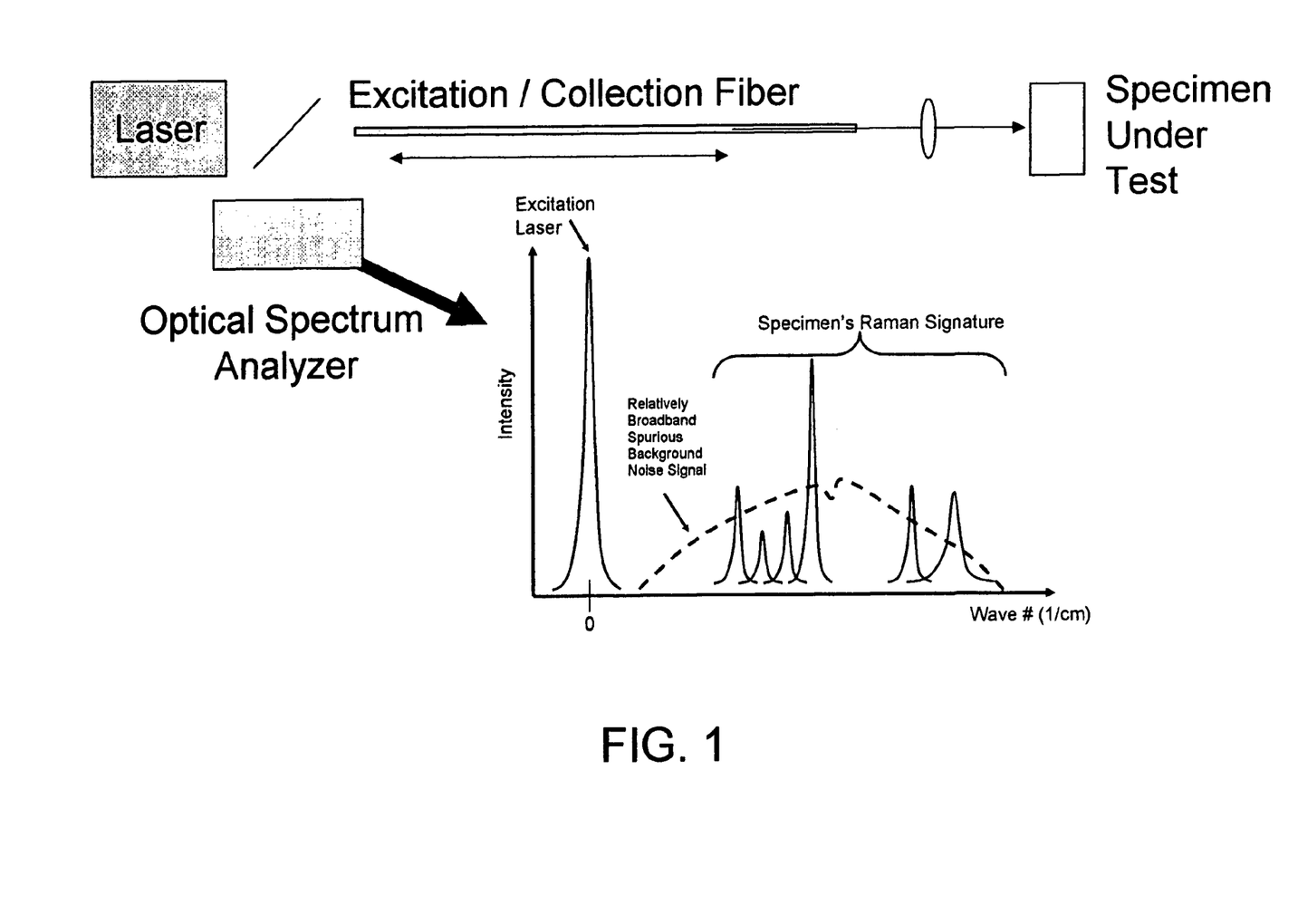
FIG. 1 is a schematic view illustrating how the Raman signature of a specimen can be diminished by the creation of a relatively broadband spurious background noise signal when using a single conventional optical fiber to both deliver the pump light to the specimen and collect the Raman signature from the specimen.

As a result, where a single conventional optical fiber is used to both deliver the pump light to the specimen and to collect the Raman signature from the specimen, the relatively broadband spurious background noise signal from the fiber is superimposed on the Raman signature of the specimen. See FIG. 1. Since the relatively broadband spurious background noise signal from the fiber tends to encompass the wavelengths associated with the specimen's Raman signature, the Raman signature is effectively obscured to some extent against the noise of the relatively broadband spurious background noise signal from the fiber. In other words, the signal-to-noise ratio of the Raman signature is effectively reduced, leading to a decrease in the sensitivity of the system and hence a reduction of specimen selectivity.

Figure 2:
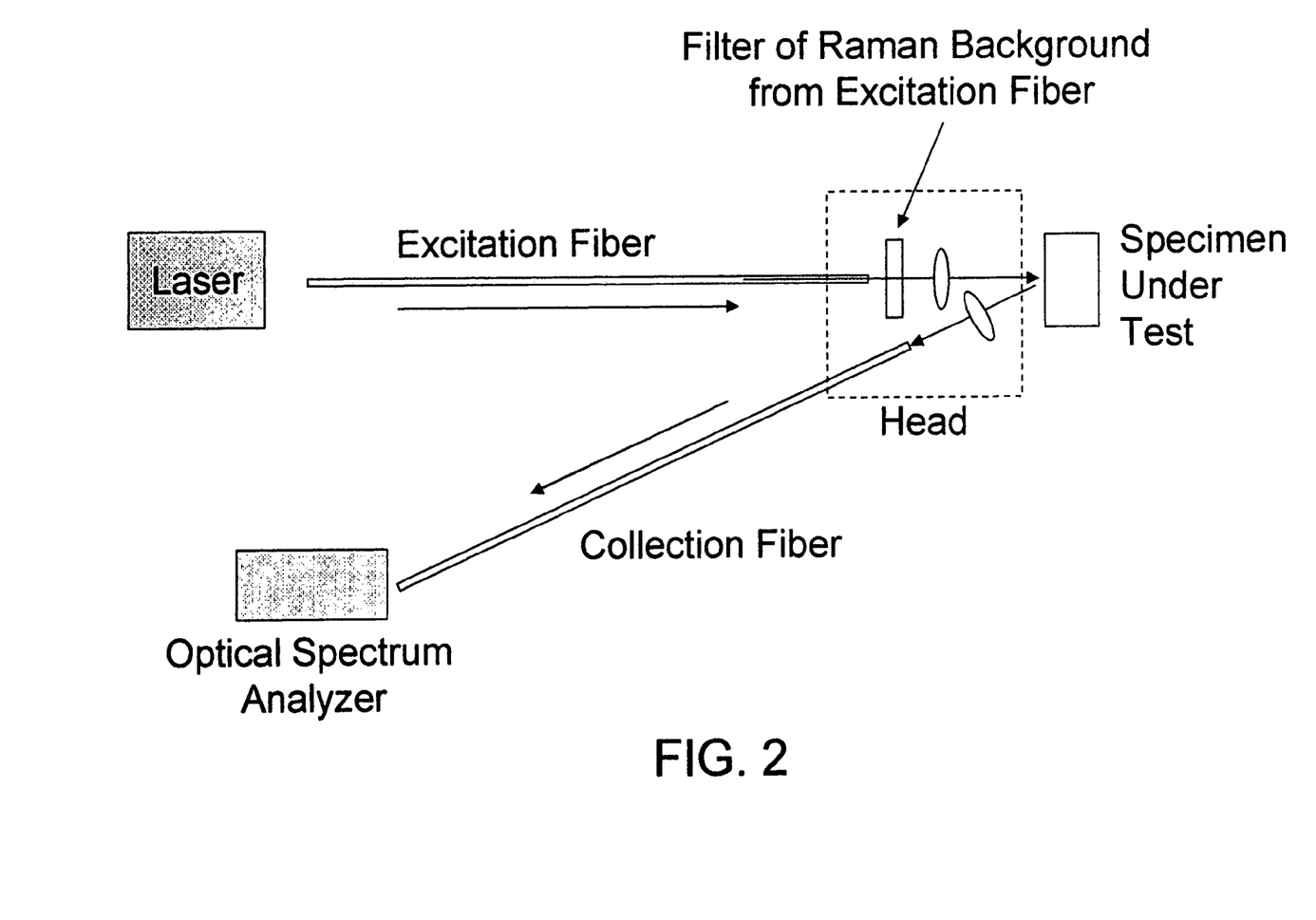
FIG. 2 is a schematic view illustrating how a relatively broadband spurious background noise signal may be isolated from the Raman signature of a specimen by using a separate excitation fiber, followed by a filter, and then a separate collection fiber.

For this reason, one optical fiber (the excitation fiber) is generally used to deliver the excitation light to the specimen, and another optical fiber (the collection fiber) is generally used to collect the Raman signature from the specimen. See FIG. 2. A filter is generally placed at the end of the excitation fiber to remove the relatively broadband spurious background noise signal induced by the high intensity pump light passing through the excitation fiber. The Raman signature coming off the specimen is picked up by the collection fiber and passed to the optical spectrum analyzer (i.e., spectrometer, computer, etc.). However, the light coming off the specimen and passing through the collection fiber does not induce a significant relatively broadband spurious background noise signal due to the diminished intensity of the light. Thus, by using one conventional optical fiber (and filter) to deliver the pump light to the specimen, and a separate conventional optical fiber to collect the Raman signature from the specimen, the Raman signature remains relatively distinct and readable. The two fibers may be geometrically separated (as shown in FIG. 2) or, alternatively, the geometry can be collinear and an arrangement of dichroic beamsplitters and filters may be used to separate the signal and excitation light.

In any case, the complexity of a two fiber and filter construction (i.e., excitation fiber, filter and collection fiber) increases the cost of the optical probe head and makes a disposable optical probe head significantly less feasible.

Accordingly, a primary object of the present invention is to provide an improved Raman spectroscopy system which overcomes the aforementioned shortcomings of currently available systems.

Another object of the present invention is to provide an improved optical probe assembly which is configured so as to avoid generating a significant relatively broadband spurious background noise signal when delivering the pump light to the specimen.

SUMMARY OF THE INVENTION

In one preferred embodiment of the present invention, there is provided an improved Raman spectroscopy system which comprises an improved optical probe assembly utilizing a single light guide to both deliver pump light to the specimen and to collect the Raman signature from the specimen, with the single light guide being constructed so as to minimize any relatively broadband spurious background noise signal when delivering pump light to the specimen. As a result, the signal-to-noise ratio of the Raman signature will remain robust even where only a single light guide is used, thereby maintaining sensitivity of the system and enhancing specimen selectivity.

In one preferred form of the invention, the optical probe assembly preferably comprises an optical guide comprising a core region and a surrounding cladding region, wherein the core region is constructed so as to minimize the creation of any relatively broadband spurious background noise signal when passing the pump light, and the cladding region is constructed so as to satisfy wave guiding reflection requirements.

The improved optical probe assembly is preferably disposable due to its simplicity.

In another form of the present invention, there is provided an optical probe assembly for conveying Raman pump light to a specimen and for conveying a Raman signature from the specimen to an optical spectrum analyzer, the optical probe assembly comprising a light guide, wherein the light guide comprises a core region and a surrounding cladding region, wherein the core region is constructed so as to minimize the creation of a relatively broadband spurious background noise signal when conveying the Raman pump light to the specimen, and the cladding region is constructed so as to satisfy the wave guiding reflection requirements of the Raman pump light and the Raman signature.

In another form of the present invention, there is provided a Raman spectroscopy system comprising:

a laser for producing Raman pump light;

an optical probe assembly for conveying the Raman pump light to a specimen and for conveying a Raman signature from the specimen to an optical spectrum analyzer, the optical probe assembly comprising a light guide, wherein the light guide comprises a core region and a surrounding cladding region, wherein the core region is constructed so as to minimize the creation of a relatively broadband spurious background noise signal when conveying the Raman pump light to the specimen, and the cladding region is constructed so as to satisfy wave guiding reflection requirements of the Raman pump light and the Raman signature; and an optical spectrum analyzer for receiving the Raman signature of a specimen and identifying and characterizing the specimen based upon the spectrum of the Raman signature.

In another form of the present invention, there is provided a method for conducting Raman spectroscopy comprising:

producing Raman pump light;

conveying the Raman pump light through an optical probe assembly to a specimen and conveying a Raman signature from the specimen through the optical probe assembly to an optical spectrum analyzer, the optical probe assembly comprising a light guide, wherein the light guide comprises a core region and a surrounding cladding region, wherein the core region is constructed so as to minimize the creation of a relatively broadband spurious background noise signal when conveying the Raman pump light to the specimen, and the cladding region is constructed so as to satisfy wave guiding reflection requirements of the Raman pump light and the Raman signature; and identifying and characterizing the specimen based upon the spectrum of the Raman signature.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein.

DETAILED DESCRIPTION OF THE PREFERRED EMBODIMENTS

Figure 3:
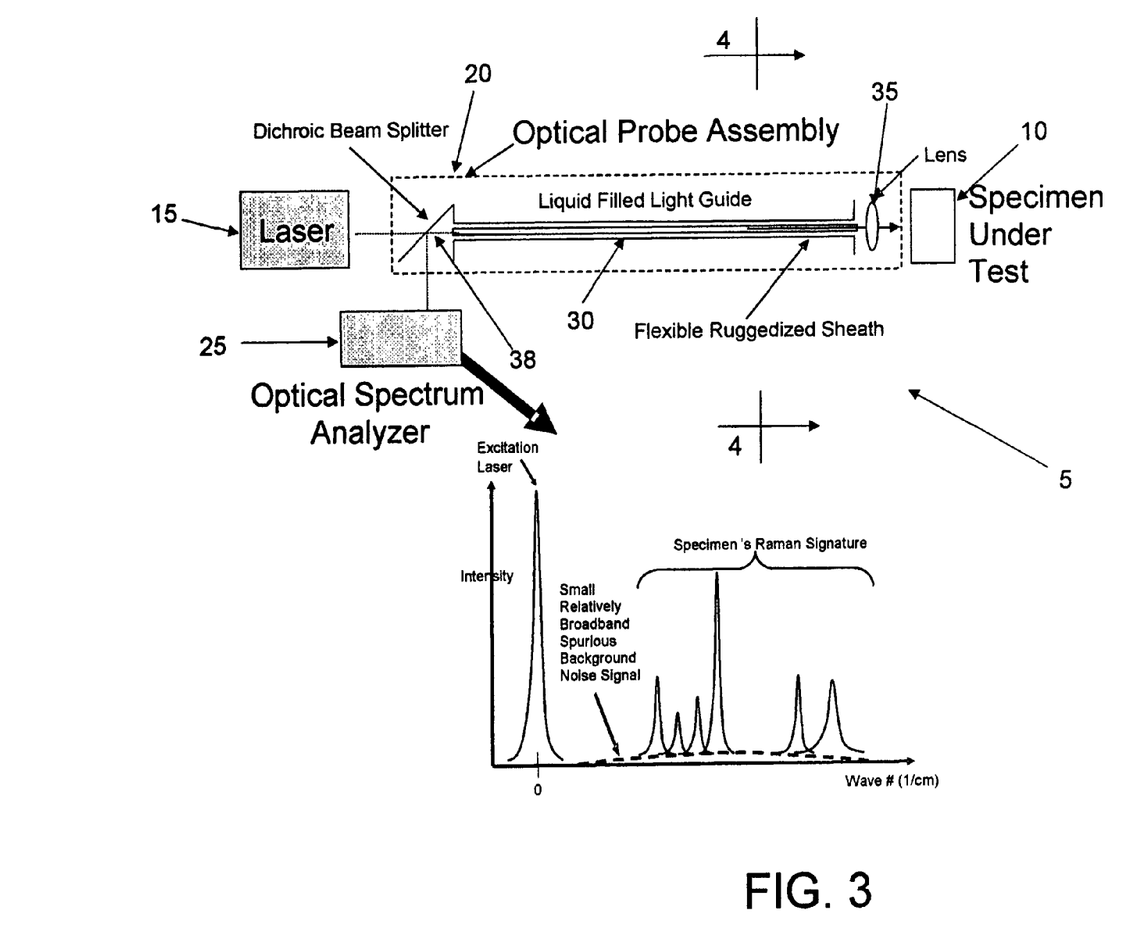
FIG. 3 is a schematic view illustrating how a single light guide may be used to both deliver pump light to the specimen and to collect the Raman signature from the specimen, wherein the single light guide is constructed so as to minimize any relatively broadband spurious background noise signal when delivering pump light to the specimen.
Figure 4:
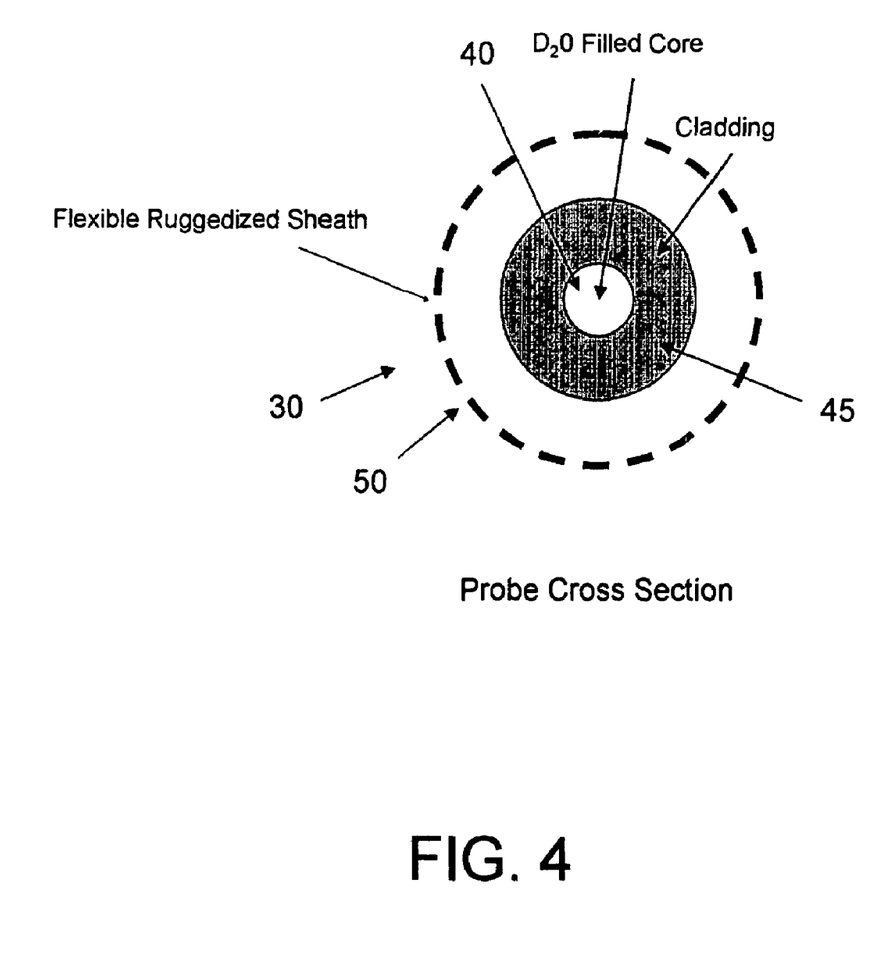
FIG. 4 is a cross-sectional view taken along line 4-4 of FIG. 3.

Looking first at FIGS. 3 and 4, there is shown a novel Raman spectroscopy system 5 for conducting remoter sensing of a specimen 10. Novel Raman spectroscopy system 5 generally comprises a laser 15 for generating the Raman pump signal, an optical probe assembly 20 for (i) delivering the Raman pump signal to the specimen, and (ii) gathering the Raman signature from the specimen, and an optical spectrum analyzer 25 for analyzing the Raman signature of the specimen so as to identify and characterize the specimen.

Laser 15 may comprise any laser suitable for use in Raman spectroscopy. By way of example but not limitation, laser 15 may comprise one or more >300 mW, 785 nm semiconductor lasers with limited linewidths (e.g., ~2 cm$^{-1}$). The output of laser 15 is delivered into the optical probe assembly 20 for delivery to the specimen.

Optical probe assembly 20 generally comprises a light guide 30 for delivering excitation (pump) light to the specimen and for collecting the Raman signature from the specimen, a lens 35 for efficient delivery of light to the specimen and for efficient collection of light from the specimen, and a dichroic beam splitter 38 for directing at least some of the returning light to optical spectrum analyzer 25.

Light guide 30 preferably comprises a core region 40 and a cladding region 45 (FIG. 4). Core region 40 preferably contains the majority of the optical field while cladding region 45 is used in the tails of the optical field. Core region 40 is constructed so as to minimize the creation of spurious background noise signals when passing the pump light and, more preferably, core region 40 is constructed so as to minimize the creation of any relatively broadband spurious background noise signal when passing the pump light. Cladding region 45 is constructed so as to satisfy wave guiding reflection requirements.

Light guide 30 preferably comprises a liquid-filled structure, e.g., a capillary structure.

In one preferred form of the invention, core region 40 comprises heavy water ($D_2O$). The "low Raman cross-section" of heavy water ($D_2O$) ensures that the high power excitation (pump) light does not generate spurious Raman signals in the region of interest (e.g., near infrared). In other words, by making core region 40 out of heavy water ($D_2O$), the pump light can be delivered from laser 15 to specimen 10 without creating a significant relatively broadband spurious background noise signal. As a result, a single light guide, i.e., the heavy water ($D_2O$) filled light guide 30, can be used to carry both the excitation laser light to specimen 10 and to collect the Raman signature from specimen 10.

Figure 5:
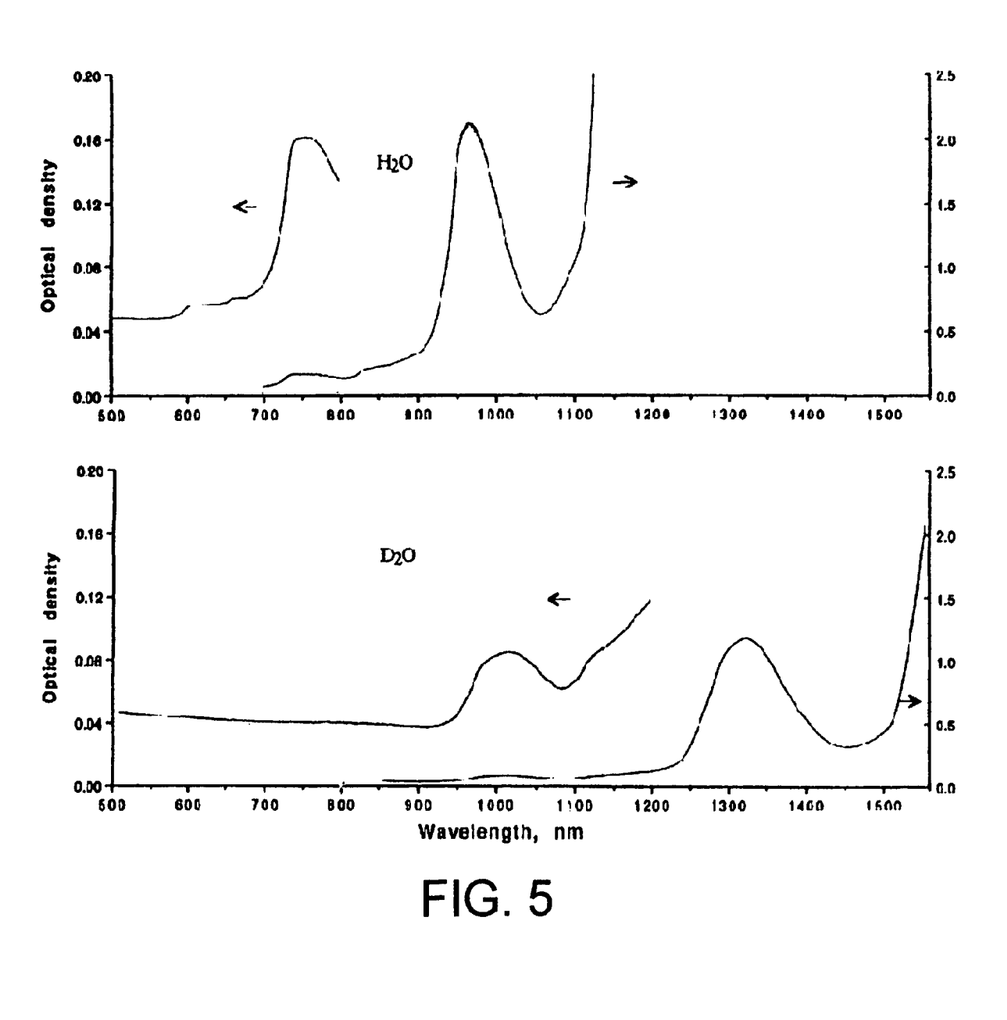
FIG. 5 is a graph comparing the loss spectrum of $D_2O$ versus $H_2O$.

Using heavy water ($D_2O$) to form the core region 40 also makes it possible to achieve low loss for both the excitation laser being delivered to specimen 10 and the Raman signature being collected from specimen 10. A plot of the loss spectrum of $D_2O$ versus $H_2O$ is shown in FIG. 5.

Thus, heavy water ($D_2O$) has the dual advantages of generating a minimal relatively broadband spurious background noise signal, and relatively little optical loss, in the wavelength range of interest (e.g., 780 nm to 1100 nm). Other solvents generally produce a substantial relatively broadband spurious background noise signal, and/or exhibit relatively high optical loss, in the wavelength range of interest (e.g., 780 nm to 1100 nm). However, the present invention is intended to encompass core regions formed out of liquids in addition to heavy water ($D_2O$) which are capable of generating a minimal relatively broadband spurious background noise signal, and relatively little optical loss, in the wavelength range of interest.

As noted above, cladding region 45 is constructed so as to satisfy wave guiding reflection requirements. Where core region 40 comprises heavy water ($D_2O$), which has an optical index of ~1.32, cladding region 45 has a cladding index of less than 1.32. Cladding region 45 may be made from a plastic material (e.g., Dupont TeflonAF or other appropriate polymers), etc.

Light guide 30 may also comprise a photonic crystal structure, with cladding region 45 comprising engineered photonic bandgap (crystal) structures.

After the return light is received by light guide 30, some of the returning light is directed through dichroic beam splitter 38 and into optical spectrum analyzer 25. The dichroic beam splitter 38 is used to spatially separate the reflected pump signal from the specimen's Raman signature.

Thus, novel light guide 30 allows the co-propagation of the high intensity laser (pump) light with the Stokes-shifted Raman signature from the specimen, while introducing a minimal relatively broadband spurious background noise signal onto the collected signature. The light can be either multimode (e.g., with a core size of ~100-200 µm and a numerical aperture of >0.3), or single-mode, depending on the spatial mode properties of the laser used.

Light guide 30 can include a ruggedized external sheath 50 for environmental protection.

Further Constructions

It is to be understood that the present invention is by no means limited to the particular constructions herein disclosed and/or shown in the drawings, but also comprises any modifications or equivalents within the scope of the invention.

What is claimed is:

1. An optical probe assembly for conveying Raman pump light to a specimen and for conveying a Raman signature from the specimen to an optical spectrum analyzer, the optical probe assembly comprising a light guide, wherein the light guide comprises:
   a core region operable to minimize the creation of a relatively broadband spurious background noise signal when conveying the Raman pump light to the specimen; and
   a cladding region surrounding the core region, the cladding region comprising a photonic crystal structure with properties selected to conform with the wave guiding reflection requirements of the Raman pump light and the Raman signature.

2. An optical probe assembly according to claim 1 wherein the light guide comprises a liquid structure.

3. An optical probe assembly according to claim 2 wherein the light guide comprises a capillary structure.

4. An optical probe assembly according to claim 2 wherein the core region comprises heavy water ($D_2O$).

5. An optical probe assembly according to claim 1 wherein the cladding region has a cladding index less that the optical index of the core region.

6. An optical probe assembly according to claim 4 wherein the cladding region has a cladding index which is less than 1.32.

7. An optical probe assembly according to claim 1 wherein the cladding region comprises an engineered photonic bandgap (crystal) structure.

8. An optical probe assembly according to claim 1 wherein the light guide further comprises an external sheath for environmental protection.

9. An optical probe assembly according to claim 1 wherein the assembly further comprises a dichroic beam splitter.

10. A Raman spectroscopy system comprising:
    a laser for producing Raman pump light;
    an optical probe assembly for conveying the Raman pump light to a specimen and for conveying a Raman signature from the specimen to an optical spectrum analyzer, the optical probe assembly comprising a light guide, wherein the light guide comprises:
       a core region operable to minimize the creation of a relatively broadband spurious background noise signal when conveying the Raman pump light to the specimen; and
       a cladding region surrounding the core region, the cladding region comprising a photonic crystal structure with properties selected to conform with the wave guiding reflection requirements of the Raman pump light and the Raman signature; and
    an optical spectrum analyzer for receiving the Raman signature of a specimen and identifying and characterizing the specimen based upon the spectrum of the Raman signature.

11. A Raman spectroscopy system according to claim 10 wherein the light guide comprises a liquid structure.

12. A Raman spectroscopy system according to claim 11 wherein the light guide comprises a capillary structure.

13. A Raman spectroscopy system according to claim 11 wherein the core region comprises heavy water ($D_2O$).

14. A Raman spectroscopy system according to claim 10 wherein the cladding region has a cladding index less that the optical index of the core region.

15. A Raman spectroscopy system according to claim 13 wherein the cladding region has a cladding index which is less than 1.32.

16. A Raman spectroscopy system according to claim 10 wherein the cladding region comprises an engineered photonic bandgap (crystal) structure.

17. A Raman spectroscopy system according to claim 10 wherein the light guide further comprises an external sheath for environmental protection.

18. A Raman spectroscopy system according to claim 10 wherein the optical probe assembly further comprises a dichroic beam splitter.

19. A method for conducting Raman spectroscopy comprising:

producing Raman pump light;

conveying the Raman pump light through an optical probe assembly to a specimen and conveying a Raman signature from the specimen through the optical probe assembly to an optical spectrum analyzer, the optical probe assembly comprising a light guide, wherein the light guide comprises:

a core region operable to minimize the creation of a relatively broadband spurious background noise signal when conveying the Raman pump light to the specimen; and a cladding region surrounding the core region, the cladding region comprising a photonic crystal structure with properties selected to conform with the wave guiding reflection requirements of the Raman pump light and the Raman signature; and identifying and characterizing the specimen based upon the spectrum of the Raman signature.

20. A method according to claim 19 wherein the light guide comprises a liquid structure.

21. A method according to claim 20 wherein the light guide comprises a capillary structure.

22. A method according to claim 20 wherein the core region comprises heavy water ($D_2O$).

23. A method according to claim 19 wherein the cladding region has a cladding index less that the optical index of the core region.

24. A method according to claim 22 wherein the cladding region has a cladding index which is less than 1.32.

25. A method according to claim 19 wherein the cladding region comprises an engineered photonic bandgap (crystal) structure.

26. A method according to claim 19 wherein the light guide further comprises an external sheath for environmental protection.

27. A method according to claim 19 wherein the optical probe assembly further comprises a dichroic beam splitter.

28. An optical probe assembly according to claim 1 wherein the light guide comprises a single-mode waveguide.

29. An optical probe assembly according to claim 1 wherein the light guide comprises a multi-mode waveguide.

30. A Raman spectroscopy system according to claim 10 wherein the light guide comprises a single-mode waveguide.

31. A Raman spectroscopy system according to claim 10 wherein the light guide comprises a multi-mode waveguide.

32. A method according to claim 19 wherein the light guide comprises a single-mode waveguide.

33. A method according to claim 19 wherein the light guide comprises a multi-mode waveguide.

* * * * *